United States Patent [19]

Amir et al.

[11] Patent Number: 5,550,583
[45] Date of Patent: Aug. 27, 1996

[54] INSPECTION APPARATUS AND METHOD

[75] Inventors: Israel Amir, Princeton; Frank P. Higgins, Ewing, both of N.J.

[73] Assignee: Lucent Technologies Inc., Murray Hill, N.J.

[21] Appl. No.: 316,745

[22] Filed: Oct. 3, 1994

[51] Int. Cl.⁶ .............................. H04N 7/18; H04N 17/00
[52] U.S. Cl. ................................ 348/126; 348/87
[58] Field of Search .................... 348/86, 87, 88, 348/92, 125, 126, 80, 91, 89, 93, 94, 95, 127–133; H04N 7/18, 17/00

[56] References Cited

U.S. PATENT DOCUMENTS

| | | | |
|---|---|---|---|
| 4,797,942 | 1/1989 | Burt | 382/41 |
| 4,817,184 | 3/1989 | Thomason et al. | 382/8 |
| 4,847,911 | 7/1989 | Morimoto et al. | 348/87 |
| 4,978,220 | 12/1990 | Abramovich et al. | 356/394 |
| 5,039,868 | 8/1991 | Kobayashi et al. | 348/87 |
| 5,182,641 | 1/1993 | Diner et al. | 348/86 |
| 5,260,779 | 11/1993 | Wasserman | 348/87 |
| 5,414,458 | 5/1995 | Harris et al. | 348/92 |

OTHER PUBLICATIONS

Sales Brochure, "VIR 100, Video Inspection and Repair System," Link Electronics GmbH, distributed by OMNI Tech International, St. Paul, Minnesota.

*Primary Examiner*—Tommy P. Chin
*Assistant Examiner*—Vu Le
*Attorney, Agent, or Firm*—Robert B. Levy

[57] ABSTRACT

Human inspection of an object (12) having a light-reflective areas (20) thereon arrayed in individual arrays (21) is enhanced by first capturing the image of selected portions of the arrays via one or more image capture devices (34). The images are processed to create a single image frame in which like portions of like arrays of light-reflective are uniformly spaced and oriented in a two-dimensional array having large scale regularity. The single image frame is then displayed on a display (48) for observation by a human operator (29). Because the displayed image frame of the light-reflective areas has large scale regularity, the operator bility to detect defects associated with missing or misaligned light-reflective areas will be enhanced.

13 Claims, 3 Drawing Sheets

5,550,583

INSPECTION APPARATUS AND METHOD

TECHNICAL FIELD

This invention relates to a technique for facilitating human inspection of an object having a generally planar surface containing a plurality of light-reflective areas.

BACKGROUND ART

Electronics manufacturers attach surface mount components to a circuit board by first printing solder paste on metallized areas on one or both major surfaces of the board. Once the paste is printed, surface mount components are placed so that each lead of a component contacts a corresponding solder paste-coated area. Thereafter, the circuit board is heated to reflow the solder paste, thereby bonding the component leads to the metallized areas.

During the component attachment process, different inspections are often performed. For instance, the board may be inspected after the solder paste is printed onto the metallized areas. The board also may be inspected after the components have been placed on the solder paste-coated metallized areas. Lastly, the board may be inspected after the solder paste has been reflowed to bond the components to the metallized areas. In the past, human operators performed each required inspection. Such inspections were found to be tedious and demanding, causing even the most careful operators to make mistakes during inspection.

In an effort to improve the process of circuit board inspection, automated inspection equipment has been developed. While such automated inspection equipment doesn't suffer from boredom and eyestrain like human operators, automated inspection equipment has been slow and expensive. More often than not, the accuracy achieved by current automated inspection equipment has not proven to be significantly better than the accuracy achieved by a human operator. Indeed, the human vision system is extremely capable of detecting irregularities in a two-dimensional or three-dimensional array of uniformly arranged and oriented items. As a human operator inspects an array of uniformly spaced items, the operator's eyes will focus quickly on those row(s) in the array containing a missing or misaligned item. Even if the array contains a large number of items, a human operator can easily detect those few that are missing and/or misaligned, provided there is large scale regularity.

Unfortunately, a typical circuit board does not have its metallized areas uniformly spaced and oriented in a two-dimensional array so as to possess large scale regularity. Most circuit boards have their metallized areas arranged in numerous individual gays. Consequently, the operator must shift his or her focus to each individual array, causing fatigue and eye strain. Thus, the arrangement of metallized areas on most circuit boards (as well as the arrangement of the component leads or pads attached thereto) is not consistent with an arrangement in which the error recognition capability of the human eye is optimized.

Thus, there is a need for an inspection technique that maximizes the capability of a human operator to detect defects.

BRIEF SUMMARY OF THE INVENTION

Briefly, a technique is disclosed for facilitating inspection of an object, such as a circuit board or the like, having a generally planar surface containing a plurality of light-reflective areas arranged in individual arrays. Depending on the stage at which such inspection is carried out, the light-reflective areas may be bare metallized areas on the circuit board. Alternatively, each light-reflective area may comprise the combination of a metallized area and a layer of solder paste printed thereon, and further may include a component lead adhered to the paste. To accomplish inspection in accordance with the invention, the images of separate portions of each individual array of light-reflective areas are captured. For example, when the individual arrays comprise orthogonal rows of light-reflective areas, the image of each row of areas of each individual array is captured. Thereafter, the individual images are processed so that the images of like portions of like arrays are oriented and arranged within a single frame in a two-dimensional array having large scale regularity. For instance, when each array comprises four orthogonal rows of the same number of light-reflective areas, the rows of the individual arrays will be re-oriented and arranged so as to be uniformly spaced in a single matrix. The image frame containing like portions of like individual arrays of light-reflective areas is then displayed, either all at once, or in successive frames, for observation by a human operator. When the like portions of the like individual linear arrays are displayed in this manner, an operator easily can detect which if any light-reflective areas are missing and/or misaligned. This is because the image frame contains the light-reflective areas arranged with large scale regularity which maximizes the operator's ability to detect defects.

DETAILED DESCRIPTION

Figure 1:
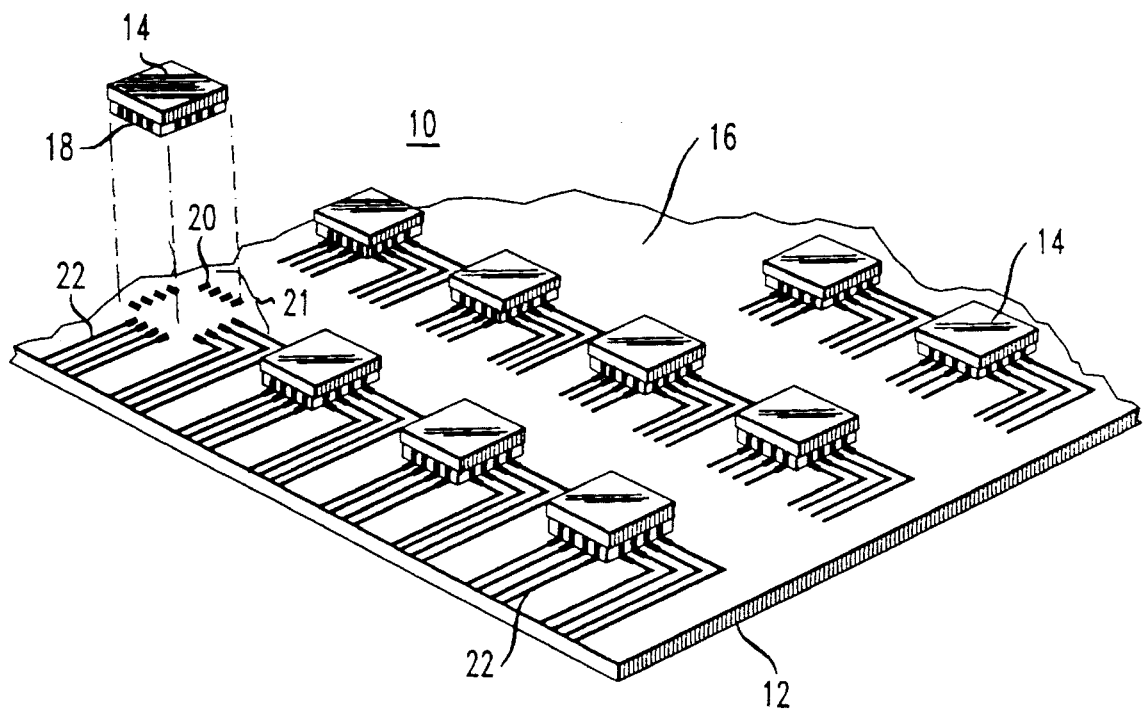
FIG. 1 a perspective view of a circuit board according to the prior art showing surface mount components mounted thereto.

FIG. 1 shows a prior-an circuit package 10 comprised of a circuit board 12 having a plurality of surface mount components 14 attached to a major surface 16 of the board. Each component 14 is attached to the board 12 by way of a solder bond between each component lead 18 and a corresponding metallized area 20 on the board surface 16. For this purpose, the metallized areas 20 are arranged in individual arrays 21, each array corresponding to the pattern of leads 18 on each component 14. In the illustrated embodiment, each component 14 is square in shape and its leads 18 are spaced equally from each other along each side of the component. Thus, each array 21 comprises four separate rows of equally spaced metallized areas 20, each row being at right angles to the others. For a component (not shown) having a different configuration of leads 18, the metallized area array 21 associated with that component will have a different arrangement. The metallized areas 20 on the board surface 16 are selectively interconnected by a set of electrical conductors (paths) 22 on the board surface.

After each component has been attached 14 to the circuit board 12, a human operator will inspect the board to detect defects such as missing or misaligned leads 18, poor lead co-planarity, as well as poor solder joints. Because of the manner in which humans process visual information, a human operator is better able to detect defects when the metallized areas 20 (as well as the leads 18 attached thereto) are arrayed in a two-dimensional array having large scale regularity. In other words, a human operator more readily can detect defects when the metallized areas 20 are equally spaced in rows that are generally equally spaced from each other. Unfortunately, few if any circuit boards 12 have their metallized areas 20 arrayed in this manner. Rather, most circuit boards 12 have their metallized areas arranged in the individual arrays 21 described earlier.

Figure 2:
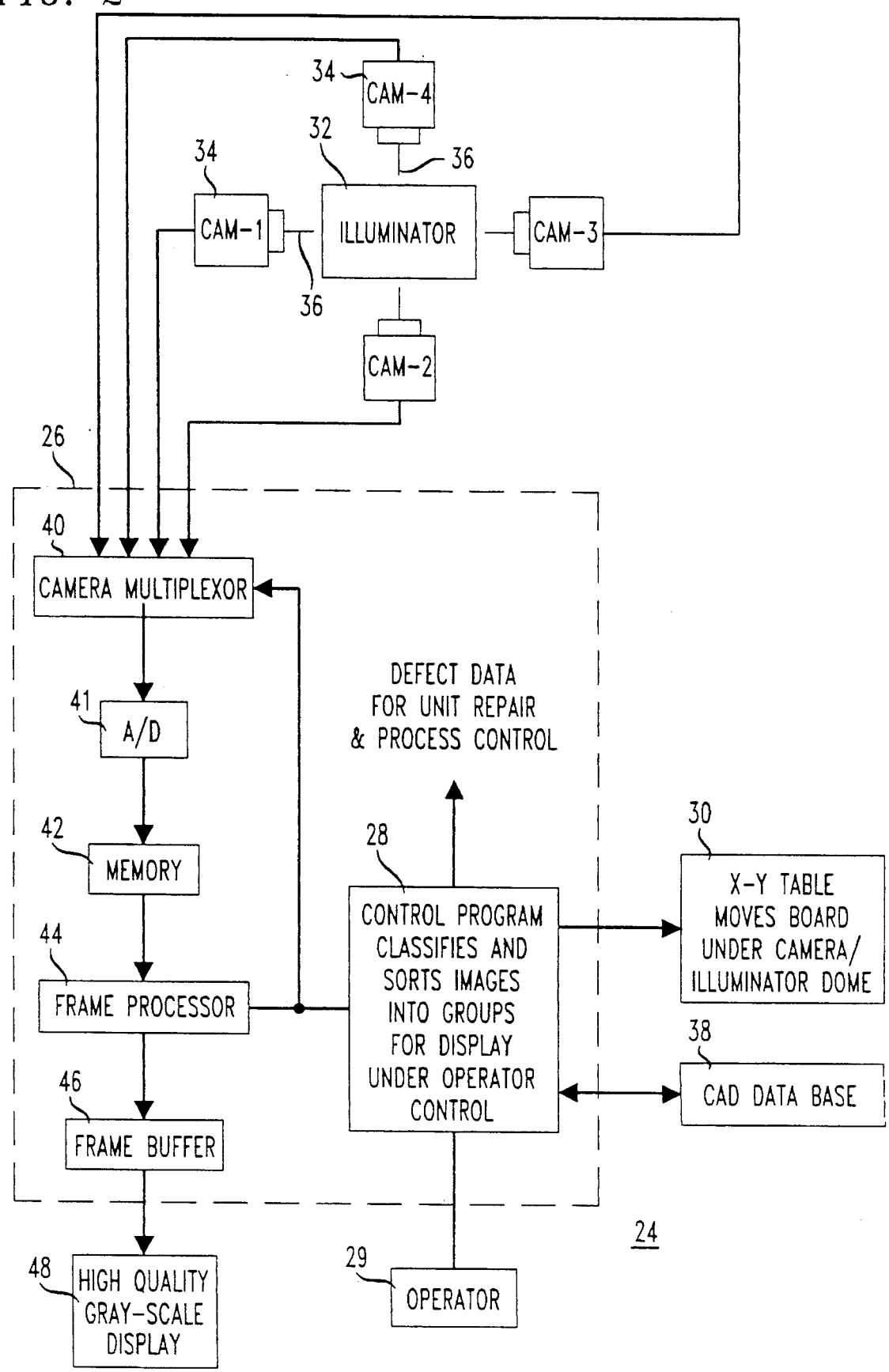
FIG. 2 is a block schematic diagram of a system, in accordance with the invention for inspecting the circuit board of FIG. 1.

Referring to FIG. 2, there is shown a system 24, in accordance with the present invention, that enhances an operator's ability to inspect the circuit board 12 by maximizing the operator's ability to process visual information. The system 24 includes an information processor 26, typically a personal computer such as a system 3333 computer available from AT&T Global Information Solutions Inc. (formerly NCR Corp.), Dayton, Ohio. To better understand the manner in which the system 24 operates, the processor 26 will be described in terms of a set of elements for performing certain functions rather than the structural details of the information processor itself. At the heart of the information processor 26 is a stored control program 28, typically stored on a magnetic disk or a similar storage media (not shown). The stored control program 28 is executed by way of one or more microprocessors (not shown). Upon execution of the stored control program 28, the information processor 26 operates to classify, sort and group images of the circuit board 12 of FIG. 1 under the direction of a human operator, schematically identified in FIG. 2 by an element 29.

In the process of classifying, sorting and grouping images, the information processor 26 controls the operation of an x-y table 30 of FIG. 2. The x-y table 30 functions to displace the circuit board 12 of FIG. 1 within an x-y plane beneath an illuminator 32 that illuminates the board. At least one, and preferably four, television cameras 34 are trained on the x-y table 30 for capturing the image of the circuit board 12 of FIG. 1. In the preferred embodiment, the four television cameras 34 are trained on the x-y table 30 so that each television camera images the circuit board 12 of FIG. 1 on the x-y table from a separate one of the four sides of the board. In this way, each camera 34 has its optical axis 36 orthogonal to each of the four rows of metallized areas 20 of FIG. 1, respectively, comprising each metallized area array 21 of FIG. 1. This is because each array 21 of FIG. 1 typically has each of its four orthogonal rows of metallized areas 20 of FIG. 1 parallel to each of the four sides, respectively, of the circuit board 12 of FIG. 1.

In practice, the optical characteristics of each camera 34 are chosen such that a single row of metallized areas 20 (see FIG. 1) within a single metallized area array 21 of FIG. 1 (as well as the leads 18 attached to such metallized areas) will typically occupy almost all of the camera's field of view. However, in practice, the field of view of each of the cameras 34 is set to provide an adequate quality for inspection while trying to maximize image matrix size. A typical image matrix may contain 20×7 images and may grow larger (or smaller) based on the nature of the circuit pack undergoing inspection. Thus, for each of the cameras 34 to image successive rows of metallized areas 20 of FIG. 1 (and the leads 18 attached thereto), the x-y table 30 must displace the circuit board 12 of FIG. 1 to locate the corresponding row of metallized areas and leads in the camera's field of view. To this end, the information processor 26 of FIG. 2 is coupled to a data base 38 of FIG. 2 that contains Computer-Aided Design (CAD) information about the circuit board 12 of FIG. 1. In particular, the data base 38 contains information about the location of each row of metallized areas 20 of FIG. 1 in each metallized area array 21 of FIG. 1. During execution of the control program 28 of FIG. 2, the processor 26 utilizes the data from the data base 38 to drive the x-y table 30 so that each camera 34 images each successive row of metallized areas 20 of FIG. 1 perpendicular to the optical axis of that camera. As may now be appreciated, employing four cameras 34, rather than a single camera, eliminates the need for any rotational movement of the circuit board in order to align each successive row of metallized areas 20 of FIG. 1 perpendicular to the optical axis 36 of a camera 34. Clearly, other arrangements, containing fewer cameras and mechanical rotation of the optical image of the board may also be provided.

The four television cameras 34 each have their outputs coupled to a camera multiplexor 40 that also comprises part of the processor 26. The camera multiplexor 40 operates under the control of the control program 28 to pass the output signal of a particular camera 34 to an analog-to-digital converter 41 that converts the camera signal to a digital signal. The output signal of the analog-to-digital converter is supplied to a memory 42 for storage. In this way, the memory 42 stores the image of the row of metallized areas 20 (and the leads 18 attached thereto) of FIG. 1 imaged by that camera 34 whose signal is passed by the multiplexor 40. The digitized camera output signals passed to the memory 42 are selected so that only the digitized camera signals representative of the images of like rows of metallized areas 20 (and the leads 18 attached thereto) are stored in the memory at one time.

For example, at a given instant, the memory 42 would store the images of the vertically oriented rows of metallized areas 20 and leads 18 (both of FIG. 1) that contain eight metallized areas (and leads) corresponding to a particular type of component 14 of FIG. 1. During the next interval, the memory 42 might store the images of the horizontally oriented rows of metallized areas 20 (and leads 18) associated with the same type of component. Thereafter, the memory 42 might store the images of the rows of metallized areas (and leads 18) associated with a different component.

The memory 42 is coupled to a frame processor 44 that also comprises part of the information processor 26. The frame processor 44 operates under the control of the control program 28 and serves to process the like images stored in the memory 42. In In particular, the frame processor 46 processes the images stored in the memory 42 to arrange the rows of metallized areas 20 of FIG. 2 (and the leads 18 attached thereto) into a single frame (image pattern). Within that single image pattern, the rows of metallized areas 20 (and the leads 18 attached thereto) are oriented and arranged in a uniformly spaced fashion to yield a single, two-dimensional array having large scale regularity.

The frame processor 44 has its output coupled to a frame buffer (46) that stores the single frame created by the frame processor. In practice, the frame buffer 46 stores 1024×768 picture elements (pixels). The frame buffer 46 has its output coupled to a high-resolution display 48 to enable the operator 29 to observe the two-dimensional array of metallized areas 20 and leads 18 of FIG. 3.

Figure 3:
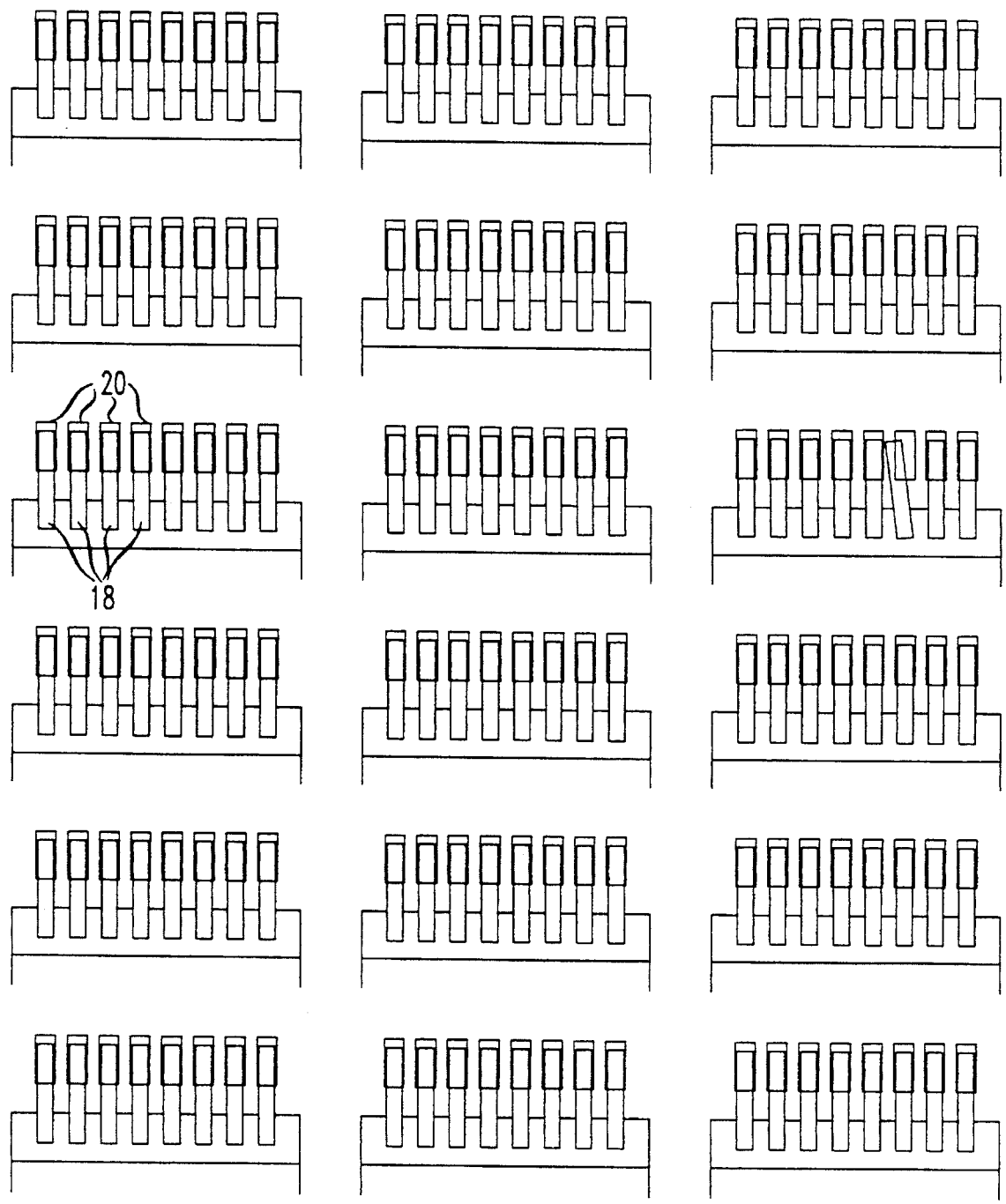
FIG. 3 is an illustration of a display frame produced by the system of FIG. 2, showing the light-reflective areas arranged in a two-dimensional array having large scale regularity.

As indicated, the two-dimensional array of the rows of metallized areas 20 and leads 18 of FIG. 3 displayed by the display 48 of FIG. 2 has large scale regularity. Thus, the ability of the operator 29 of FIG. 2 to detect defects in the image will be maximized because a human's ability to detect defects in an array is maximized when there is large scale regularity as is the case with the array of FIG. 3. Upon detection of a defect, the operator 29 of FIG. 2 alerts the control program 28 of FIG. 2, typically by operating a "mouse" not shown to highlight or otherwise indicate the area where the defect has been detected. This information would then be correlated, via the CAD data base 38, to determine which lead 18 of which component 14 of FIG. 1 was affected.

The defect detection scheme described above would be repeated for each different type or class of components 14 (see FIG. 1). Thus, for example, all of the rows of metallized areas 20 and leads 18 (both of FIG. 1) associated with one type of component 14 (see FIG. 1) may be inspected first. Then, the metallized areas 20 and leads 18 of the next type of component may be inspected and so on, until all of the metallized areas and leads associated with the various components have been examined.

As described, a whole frame, comprising the vertical and horizontal rows of metallized areas 20 of a single component 14, are typically displayed at once. However, rather than display a whole frame at once, the display could be scrolled so that successive new rows (representing a horizontal or vertical row of metallized areas 20) may be displayed one at a time. As each new row is displayed, that row is marked to alert the operator of its presence. The total amount of time each new row is displayed would be similar to the time that all of the rows are displayed during a static (non-scrolling) display. If an operator needs additional time to analyze a new row, the operator can continue to perform such analysis until the row under observation is filled by a new row. The current row could be marked by a small space between the row and the one behind it, or by highlighting it. By marking each row, an operator can scroll backward or forward one row at a time, rather than frame by frame.

The inspection process has been described for a circuit board 12 (see FIG. 1) having components 14 placed thereon. It should be appreciated that the technique of the invention is equally applicable for the boards 12 themselves, and for boards which have their metallized areas 20 coated with solder paste. Moreover, the process is applicable for other processes wherein inspection is desired of an object having a plurality of light-reflective areas arrayed on one or more generally planar surfaces.

In practice, the images displayed in each frame (i.e., the horizontal and vertical rows of metallized areas) are displayed in a two-dimensional array. However, there are instances when a three-dimensional presentation would provide a superior performance. For example, when the leads 18 are lifted from the surface 16 of FIG. 1, it may be very difficult to detect such a defect using two-dimensional imagery. Thus, three-dimensional imaging may be crucial to inspection. This can be accomplished by integrating stereo imaging and, for example, by color coding and color or LCD glasses. This approach is the same as described except that the images displayed would appear three-dimensional.

While the images displayed in each frame are typically captured by the television cameras 34–34, this need not always be the case. For example, each of the cameras 34–34 could be replaced by an x-ray sensor when object under inspection is exposed to x-ray radiation to detect defects not visible by other means. Other types of sensing devices could likewise be used.

It is to be understood that the above-described embodiments are merely illustrative of the principles of the invention. Various modifications and changes may be made thereto by those skilled in the art which will embody the principles of the invention and fall within the spirit and scope thereof.

What is claimed is:

1. A method of facilitating inspection of an object having a generally planar surface containing a plurality of light-reflective area arranged in individual arrays, comprising the steps of:

(a) capturing an image of each of a plurality selected portions of each array of light-reflective areas;

(b) arranging the images of like portions of like arrays in a single frame such that the light-reflective areas in the frame are oriented and arranged separately in a two-dimensional array having large scale regularity to de-randomize and de-locate the arrays of light-reflective areas so that the light-reflective areas lie in at least one row and generally exhibit the same orientation from row-to-row; and (c) displaying the frame on a display device for observation and inspection by a human operator to detect which if any light-reflective areas are defective, missing or misaligned.

2. The method according to claim 1 wherein the steps (b) and (c) are repeated until the selected portions of the arrays have all been displayed for inspection.

3. The method according to claim 1 wherein at least some of the arrays are comprised of rows of light-reflective areas arranged orthogonally to each other and wherein the selected portion of each area whose image is captured corresponds to one of the rows of said array.

4. The method according to claim 1 further including the step of storing the images in a memory.

5. The method according to claim 1 wherein the step of capturing the image of each of a plurality of selected portions of each array comprises the steps of:

training at least one television camera onto the object; and imparting a relative movement between the object and the camera in accordance with the locations of the arrays of light-reflective areas so that each selected portion of each array lines up within a field of view of the camera.

6. The method according to claim 1 wherein the light-reflective areas in the frame are displayed simultaneously.

7. The method according to claim 1 wherein the light-reflective areas in the frame are displayed in succession.

8. The method according to claim 1 wherein the images in the frame are two-dimensional images.

9. The method according to claim 1 wherein the images in the frame are three-dimensional images.

10. The method according to claim 1 wherein the display is scrolled.

11. Apparatus for facilitating inspection of an object having a generally planar surface containing light-reflective areas arranged in individual arrays, comprising:

at least one image-capture device for capturing the image of at least one selected portion of at least one array of light-reflective array;

means for imparting a relative motion between the image-capture device and the object so that the image capture device captures successive selected portions of successive arrays of light-reflective arrays;

means for arranging the images captured by the image-capture device so that the images of like portions of like arrays are oriented and arranged separately in a single-image frame in which the light-reflective areas are arrayed in a two-dimensional array having large scale regularity to de-randomize and de-locate the arrays of light-reflective areas so that the light-reflective areas lie in at least one row and generally exhibit the same orientation from row-to-row; and a display coupled to the means for arranging the images for displaying the single image frame for observation by an operator.

12. The apparatus according to claim 11 wherein there are four image-capture devices, each trained on one of four sides of the object.

13. The apparatus according to claim 11 wherein the means for arranging the images comprises:

frame-processing means under the control of a control program which, when executed, classifies, sorts, orients and groups images to yield the single image frame; and a frame buffer for storing the single image frame generated by the frame buffer.

* * * * *